United States Patent
McIntyre et al.

(10) Patent No.: US 6,887,978 B2
(45) Date of Patent: May 3, 2005

(54) VANILLOID RECEPTOR

(75) Inventors: Peter McIntyre, London (GB); Iain Fraser James, London (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/128,853

(22) Filed: Apr. 23, 2002

(65) Prior Publication Data

US 2003/0003536 A1 Jan. 2, 2003

Related U.S. Application Data

(63) Continuation of application No. 09/533,220, filed on Mar. 23, 2000, now Pat. No. 6,406,908.

(30) Foreign Application Priority Data

Mar. 26, 1999 (GB) ............................................. 9907097

(51) Int. Cl.⁷ .......................... C07K 14/00; C12P 21/06; A61K 38/00
(52) U.S. Cl. ........................... 530/350; 435/69.1; 514/2
(58) Field of Search ........................ 530/350; 435/69.1; 514/2

(56) References Cited

U.S. PATENT DOCUMENTS

| | | |
|---|---|---|
| 5,714,666 A | 2/1998 | Pritchette et al. |
| 6,239,267 B1 | 5/2001 | Duckworth et al. |
| 6,335,180 B1 * | 1/2002 | Julius et al. ............... 435/69.1 |

FOREIGN PATENT DOCUMENTS

| | | |
|---|---|---|
| EP | 0 943 683 A1 | 9/1999 |
| EP | 0 953 638 A1 | 11/1999 |
| WO | WO 99/09140 | 2/1999 |
| WO | WO 00/37765 | 7/1999 |
| WO | WO 99/37675 | 7/1999 |
| WO | WO 99/46377 | 9/1999 |
| WO | WO 00/22121 | 4/2000 |
| WO | WO 00/29577 | 5/2000 |
| WO | WO 00/32766 | 5/2000 |
| WO | WO 00/63415 | 10/2000 |

OTHER PUBLICATIONS

Caterina et al., Nature, vol. 389, "The capsaicin receptor: a heat–activated ion channel in the pain pathway," pp. 816–824 (1997).
Suzuki et al., Journal of Biological Chemistry, vol. 274 (10), "Cloning of a Stretch–inhibitable Nonselective Cation Channel," pp. 6330–6335 (1999).

* cited by examiner

*Primary Examiner*—Janet Andres
(74) *Attorney, Agent, or Firm*—E. Jay Wilusz, Jr.

(57) ABSTRACT

The isolated nucleic acid encoding human vanilloid receptor, said receptor, its preparation, cells expressing said receptor and an assay for testing compounds for their potential to decrease pain in humans. The receptor is involved in detection of noxious stimuli in mammalian organisms.

1 Claim, No Drawings

SEQUENCE LISTING

<160> NUMBER OF SEQ ID NOS: 4

<210> SEQ ID NO 1
<211> LENGTH: 3463
<212> TYPE: DNA
<213> ORGANISM: Homo sapiens
<220> FEATURE:
<221> NAME/KEY: CDS
<222> LOCATION: (359)..(2875)

<400> SEQUENCE: 1

```
cccccagtt ttacactttt acttcccggt cgtatattgt gtgaaattgt gagcggaata      60 cccatttca cacaaggaac cagtttatcc tttgattacg ccaagctcga aattacccc      120 tcattaaaag ggaacaaaag ttggagctcg cgcgcctgca ggtcgacact agtggatcca     180
aagaattcgg cacgagccgg gcccgggacc ccacggaggc ggggagacca ctcttctccc     240
acacgagccc agctctccct tcgagtagca accgccttca agctcacaag cacccgtggg    300
```

-continued

```
cctggggtgt gcctgcgtct agctggttgc acactgggcc acagaggatc cagcaagg          358 atg aag aaa tgg agc agc aca gac ttg ggg gca gct gcg gac cca ctc          406
Met Lys Lys Trp Ser Ser Thr Asp Leu Gly Ala Ala Ala Asp Pro Leu
 1               5                  10                  15 caa aag gac acc tgc cca gac ccc ctg gat gga gac cct aac tcc agg          454
Gln Lys Asp Thr Cys Pro Asp Pro Leu Asp Gly Asp Pro Asn Ser Arg
             20                  25                  30 cca cct cca gcc aag ccc cag ctc tcc acg gcc aag agc cgc acc cgg          502
Pro Pro Pro Ala Lys Pro Gln Leu Ser Thr Ala Lys Ser Arg Thr Arg
         35                  40                  45 ctc ttt ggg aag ggt gac tcg gag gag gct ttc ccg gtg gat tgc cct          550
Leu Phe Gly Lys Gly Asp Ser Glu Glu Ala Phe Pro Val Asp Cys Pro
     50                  55                  60 cac gag gaa ggt gag ctg gac tcc tgc ccg acc atc aca gtc agc cct          598
His Glu Glu Gly Glu Leu Asp Ser Cys Pro Thr Ile Thr Val Ser Pro
 65                  70                  75                  80 gtt atc acc atc cag agg cca gga gac ggc ccc acc ggt gcc agg ctg          646
Val Ile Thr Ile Gln Arg Pro Gly Asp Gly Pro Thr Gly Ala Arg Leu
                 85                  90                  95 ctg tcc cag gac tct gtc gcc gcc agc acc gag aag acc ctc agg ctc          694
Leu Ser Gln Asp Ser Val Ala Ala Ser Thr Glu Lys Thr Leu Arg Leu
             100                 105                 110 tat gat cgc agg agt atc ttt gaa gcc gtt gct cag aat aac tgc cag          742
Tyr Asp Arg Arg Ser Ile Phe Glu Ala Val Ala Gln Asn Asn Cys Gln
         115                 120                 125 gat ctg gag agc ctg ctg ctc ttc ctg cag aag agc aag aag cac ctc          790
Asp Leu Glu Ser Leu Leu Leu Phe Leu Gln Lys Ser Lys Lys His Leu
     130                 135                 140 aca gac aac gag ttc aaa gac cct gag aca ggg aag acc tgt ctg ctg          838
Thr Asp Asn Glu Phe Lys Asp Pro Glu Thr Gly Lys Thr Cys Leu Leu
145                 150                 155                 160 aaa gcc atg ctc aac ctg cac gac gga cag aac acc acc atc ccc ctg          886
Lys Ala Met Leu Asn Leu His Asp Gly Gln Asn Thr Thr Ile Pro Leu
                 165                 170                 175 ctc ctg gag atc gcg cgg caa acg gac agc ctg aag gag ctt gtc aac          934
Leu Leu Glu Ile Ala Arg Gln Thr Asp Ser Leu Lys Glu Leu Val Asn
             180                 185                 190 gcc agc tac acg gac agc tac tac aag ggc cag aca gca ctg cac atc          982
Ala Ser Tyr Thr Asp Ser Tyr Tyr Lys Gly Gln Thr Ala Leu His Ile
         195                 200                 205 gcc atc gag aga cgc aac atg gcc ctg gtg acc ctc ctg gtg gag aac          1030
Ala Ile Glu Arg Arg Asn Met Ala Leu Val Thr Leu Leu Val Glu Asn
     210                 215                 220 gga gca gac gtc cag gct gcg gcc cat ggg gac ttc ttt aag aaa acc          1078
Gly Ala Asp Val Gln Ala Ala Ala His Gly Asp Phe Phe Lys Lys Thr
225                 230                 235                 240 aaa ggg cgg cct gga ttc tac ttc ggt gaa ctg ccc ctg tcc ctg gcc          1126
Lys Gly Arg Pro Gly Phe Tyr Phe Gly Glu Leu Pro Leu Ser Leu Ala
                 245                 250                 255 gcg tgc acc aac cag ctg ggc atc gtg aag ttc ctg ctg cag aac tcc          1174
Ala Cys Thr Asn Gln Leu Gly Ile Val Lys Phe Leu Leu Gln Asn Ser
             260                 265                 270 tgg cag acg gcc gac atc agc gcc agg gac tcg gtg ggc aac acg gtg          1222
Trp Gln Thr Ala Asp Ile Ser Ala Arg Asp Ser Val Gly Asn Thr Val
         275                 280                 285 ctg cac gcc ctg gtg gag gtg gcc gac aac acg gcc gac aac acg aag          1270
Leu His Ala Leu Val Glu Val Ala Asp Asn Thr Ala Asp Asn Thr Lys
     290                 295                 300 ttt gtg acg agc atg tac aat gag att ctg atc ctg ggg gcc aaa ctg          1318
```

-continued

```
Phe Val Thr Ser Met Tyr Asn Glu Ile Leu Ile Leu Gly Ala Lys Leu
305                 310                 315                 320 cac ccg acg ctg aag ctg gag gag ctc acc aac aag aag gga atg atg      1366
His Pro Thr Leu Lys Leu Glu Glu Leu Thr Asn Lys Lys Gly Met Met
            325                 330                 335 ccg ctg gct ctg gca gct ggg acc ggg aag atc ggg gtc ttg gcc tat      1414
Pro Leu Ala Leu Ala Ala Gly Thr Gly Lys Ile Gly Val Leu Ala Tyr
                340                 345                 350 att ctc cag cgg gag atc cag gag ccc gag tgc agg cac ctg tcc agg      1462
Ile Leu Gln Arg Glu Ile Gln Glu Pro Glu Cys Arg His Leu Ser Arg
            355                 360                 365 aag ttc acc gag tgg gcc tac ggg ccc gtg cac tcc tcg ctg tac gac      1510
Lys Phe Thr Glu Trp Ala Tyr Gly Pro Val His Ser Ser Leu Tyr Asp
370                 375                 380 ctg tcc tgc atc gac acc tgc gag aag aac tcg gtg ctg gag gtg atc      1558
Leu Ser Cys Ile Asp Thr Cys Glu Lys Asn Ser Val Leu Glu Val Ile
385                 390                 395                 400 gcc tac agc agc agc gag acc cct aat cgc cac gac atg ctc ttg gtg      1606
Ala Tyr Ser Ser Ser Glu Thr Pro Asn Arg His Asp Met Leu Leu Val
                405                 410                 415 gag ccg ctg aac cga ctc ctg cag gac aag tgg gac aga ttc gtc aag      1654
Glu Pro Leu Asn Arg Leu Leu Gln Asp Lys Trp Asp Arg Phe Val Lys
            420                 425                 430 cgc atc ttc tac ttc aac ttc ctg gtc tac tgc ctg tac atg atc atc      1702
Arg Ile Phe Tyr Phe Asn Phe Leu Val Tyr Cys Leu Tyr Met Ile Ile
            435                 440                 445 ttc acc atg gct gcc tac tac agg ccc gtg gat ggc ttg cct ccc ttt      1750
Phe Thr Met Ala Ala Tyr Tyr Arg Pro Val Asp Gly Leu Pro Pro Phe
450                 455                 460 aag atg gaa aaa act gga gac tat ttc cga gtt act gga gag atc ctg      1798
Lys Met Glu Lys Thr Gly Asp Tyr Phe Arg Val Thr Gly Glu Ile Leu
465                 470                 475                 480 tct gtg tta gga gga gtc tac ttc ttt ttc cga ggg att cag tat ttc      1846
Ser Val Leu Gly Gly Val Tyr Phe Phe Phe Arg Gly Ile Gln Tyr Phe
                485                 490                 495 ctg cag agg cgg ccg tcg atg aag acc ctg ttt gtg gac agc tac agt      1894
Leu Gln Arg Arg Pro Ser Met Lys Thr Leu Phe Val Asp Ser Tyr Ser
            500                 505                 510 gag atg ctt ttc ttt ctg cag tca ctg ttc atg ctg gcc acc gtg gtg      1942
Glu Met Leu Phe Phe Leu Gln Ser Leu Phe Met Leu Ala Thr Val Val
            515                 520                 525 ctg tac ttc agc cac ctc aag gag tat gtg gct tcc atg gta ttc tcc      1990
Leu Tyr Phe Ser His Leu Lys Glu Tyr Val Ala Ser Met Val Phe Ser
530                 535                 540 ctg gcc ttg ggc tgg acc aac atg ctc tac tac acc cgc ggt ttc cag      2038
Leu Ala Leu Gly Trp Thr Asn Met Leu Tyr Tyr Thr Arg Gly Phe Gln
545                 550                 555                 560 cag atg ggc atc tat gcc gtc atg ata gag aag atg atc ctg aga gac      2086
Gln Met Gly Ile Tyr Ala Val Met Ile Glu Lys Met Ile Leu Arg Asp
                565                 570                 575 ctg tgc cgt ttc atg ttt gtc tac atc gtc ttc ttg ttc ggg ttt tcc      2134
Leu Cys Arg Phe Met Phe Val Tyr Ile Val Phe Leu Phe Gly Phe Ser
            580                 585                 590 aca gcg gtg gtg acg ctg att gaa gac ggg aag aat gac tcc ctg ccg      2182
Thr Ala Val Val Thr Leu Ile Glu Asp Gly Lys Asn Asp Ser Leu Pro
            595                 600                 605 tct gag tcc acg tcg cac agg tgg cgg ggg cct gcc tgc agg ccc ccc      2230
Ser Glu Ser Thr Ser His Arg Trp Arg Gly Pro Ala Cys Arg Pro Pro
610                 615                 620
```

-continued

| | |
|---|---|
| gat agc tcc tac aac agc ctg tac tcc acc tgc ctg gag ctg ttc aag<br>Asp Ser Ser Tyr Asn Ser Leu Tyr Ser Thr Cys Leu Glu Leu Phe Lys<br>625                         630                            635                            640 | 2278 |
| ttc acc atc ggc atg ggc gac ctg gag ttc act gag aac tat gac ttc<br>Phe Thr Ile Gly Met Gly Asp Leu Glu Phe Thr Glu Asn Tyr Asp Phe<br>                      645                            650                         655 | 2326 |
| aag gct gtc ttc atc atc ctg ctg gcc tat gta att ctc acc tac<br>Lys Ala Val Phe Ile Ile Leu Leu Ala Tyr Val Ile Leu Thr Tyr<br>660                        665                        670 | 2374 |
| atc ctc ctg ctc aac atg ctc atc gcc ctc atg ggt gag act gtc aac<br>Ile Leu Leu Leu Asn Met Leu Ile Ala Leu Met Gly Glu Thr Val Asn<br>675                         680                            685 | 2422 |
| aag atc gca cag gag agc aag aac atc tgg aag ctg cag aga gcc atc<br>Lys Ile Ala Gln Glu Ser Lys Asn Ile Trp Lys Leu Gln Arg Ala Ile<br>          690                        695                         700 | 2470 |
| acc atc ctg gac acg gag aag agc ttc ctt aag tgc atg agg aag gcc<br>Thr Ile Leu Asp Thr Glu Lys Ser Phe Leu Lys Cys Met Arg Lys Ala<br>705                         710                            715                        720 | 2518 |
| ttc cgc tca ggc aag ctg ctg cag gtg ggg tac aca cct gat ggc aag<br>Phe Arg Ser Gly Lys Leu Leu Gln Val Gly Tyr Thr Pro Asp Gly Lys<br>                    725                        730                         735 | 2566 |
| gac gac tac cgg tgg tgc ttc agg gtg gac gag gtg aac tgg acc acc<br>Asp Asp Tyr Arg Trp Cys Phe Arg Val Asp Glu Val Asn Trp Thr Thr<br>               740                        745                        750 | 2614 |
| tgg aac acc aac gtg ggc atc atc aac gaa gac ccg ggc aac tgt gag<br>Trp Asn Thr Asn Val Gly Ile Ile Asn Glu Asp Pro Gly Asn Cys Glu<br>             755                        760                        765 | 2662 |
| ggc gtc aag cgc acc ctg agc ttc tcc ctg cgg tca agc aga gtt tca<br>Gly Val Lys Arg Thr Leu Ser Phe Ser Leu Arg Ser Ser Arg Val Ser<br>770                         775                        780 | 2710 |
| ggc aga cac tgg aag aac ttt gcc ctg gtc ccc ctt tta aga gag gca<br>Gly Arg His Trp Lys Asn Phe Ala Leu Val Pro Leu Leu Arg Glu Ala<br>785                         790                        795                        800 | 2758 |
| agt gct cga gat agg cag tct gct cag ccc gag gaa gtt tat ctg cga<br>Ser Ala Arg Asp Arg Gln Ser Ala Gln Pro Glu Glu Val Tyr Leu Arg<br>               805                        810                        815 | 2806 |
| cag ttt tca ggg tct ctg aag cca gag gac gct gag gtc ttc aag agt<br>Gln Phe Ser Gly Ser Leu Lys Pro Glu Asp Ala Glu Val Phe Lys Ser<br>             820                        825                        830 | 2854 |
| cct gcc gct tcc ggg gag aag tgaggacgtc acgcagacag cactgtcaac<br>Pro Ala Ala Ser Gly Glu Lys<br>             835 | 2905 |
| actgggcctt aggagacccc gttgccacgg ggggctgctg agggaacacc agtgctctgt | 2965 |
| cagcagcctg gcctggtctg tgcctgccca gcatgttccc aaatctgtgc tggacaaact | 3025 |
| gtgggaaagc gttcttggaa gcatgggag tgatgtacat ccaaccgtca ctgtccccaa | 3085 |
| gtgaatctcc taacagactt tcaggttttt actcacttta ctaaacagtg tggatggtca | 3145 |
| gtctctactg ggacatgtta ggcccttgtt ttctttgatt ttattctttt ttttgagaca | 3205 |
| gaatttcact cttctcgccc aggctggaat gcagtggcac aattttggct ccctgcaacc | 3265 |
| tccgcctcct ggattccagc aattctcctg cctcggcttc ccaagtagct gggattacag | 3325 |
| gcacgtgcca ccatgtctgg ctaattttt ggattttttt aataaaaatg ggggttcgcc | 3385 |
| atgttggcca ggctggtctc gaactcctga ccttagggga tccccccacc ttgggcctcc | 3445 |
| caaagggctg ggaataca | 3463 |

<210> SEQ ID NO 2
<211> LENGTH: 839

```
<212> TYPE: PRT
<213> ORGANISM: Homo sapiens

<400> SEQUENCE: 2

Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
        50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Met
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400
```

-continued

```
Ala Tyr Ser Ser Ser Glu Thr Pro Asn Arg His Asp Met Leu Leu Val
            405                 410                 415
Glu Pro Leu Asn Arg Leu Leu Gln Asp Lys Trp Asp Arg Phe Val Lys
        420                 425                 430
Arg Ile Phe Tyr Phe Asn Phe Leu Val Tyr Cys Leu Tyr Met Ile Ile
            435                 440                 445
Phe Thr Met Ala Ala Tyr Tyr Arg Pro Val Asp Gly Leu Pro Pro Phe
    450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
            515                 520                 525
Leu Tyr Phe Ser His Leu Lys Glu Tyr Val Ala Ser Met Val Phe Ser
    530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
            580                 585                 590
Thr Ala Val Val Thr Leu Ile Glu Asp Gly Lys Asn Asp Ser Leu Pro
            595                 600                 605
Ser Glu Ser Thr Ser His Arg Trp Arg Gly Pro Ala Cys Arg Pro Pro
    610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
            675                 680                 685
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
    770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Glu Val Tyr Leu Arg
                805                 810                 815
```

-continued

```
Gln Phe Ser Gly Ser Leu Lys Pro Glu Asp Ala Glu Val Phe Lys Ser
            820                 825                 830
Pro Ala Ala Ser Gly Glu Lys
        835

<210> SEQ ID NO 3
<211> LENGTH: 5155
<212> TYPE: DNA
<213> ORGANISM: Homo sapiens

<400> SEQUENCE: 3 aagcttttg caaaagccta ggaaaaaagc ctcctcacta cttctggaat agctcagagg      60
ccgaggcggc ctcggcctct gcataaataa aaaaaattag tcagccatgg ggcggagaat    120
gggcggaact gggcggagtt aggggcggga tgggcggagt taggggcggg actatggttg    180
ctgactaatt gagatgcatg ctttgcatac ttctgcctgc tggggagcct ggggactttc    240
cacacctggt tgctgactaa ttgagatgca tgctttgcat acttctgcct gctggggagc    300
ctggggactt ccacaccct aactgacaca cattccacag gatccggtcg cgcgaatttc    360
gagcggtgtt ccgcggtcct cctcgtatag aaactcggac cactctgaga cgaaggctcg    420
cgtccaggcc agcacgaagg aggctaagtg ggaggggtag cggtcgttgt ccactagggg    480
gtccactcgc tccagggtgt gaagacacat gtcgccctct tcggcatcaa ggaaggtgat    540
tggtttatag gtgtaggcca cgtgaccggg tgttcctgaa gggggggctat aaaaggggggt    600 gggggcgcgt tcgtcctcac tctcttccgc atcgctgtct gcgagggcca gctgttgggc    660
tcgcggttga ggacaaactc ttcgcggtct ttccagtact cttggatcgg aaacccgtcg    720
gcctccgaac ggtactccgc caccgaggga cctgagcgag tccgcatcga ccggatcgga    780
aaacctctcg actgttgggg tgagtactcc ctctcaaaag cgggcatgac ttctgcgcta    840
agattgtcag tttccaaaaa cgaggaggat ttgatattca cctggcccgc ggtgatgcct    900
ttgagggtgg ccgcgtccat ctggtcagaa agacaatct tttgttgtc aagcttgagg     960 tgtggcaggc ttgagatctg gccatacact tgagtgacaa tgacatccac tttgcctttc   1020
tctccacagg tgtccactcc caggtccaac tgcaggtcga ctctagagga tccccggggta   1080 ccgagctcga attccgggggg gggggggggg ggggacagct cagggctgcg atttcgcgcc   1140
aaacttgacg gcaatcctag cgtgaaggct ggtaggattt tatccccgct gccatcatgg   1200
ttcgaccatt gaactgcatc gtcgccgtgt cccaaaatat ggggattggc aagaacggag   1260
acctaccctg gcctccgctc aggaacgagt tcaagtactt ccaaagaatg accacaacct   1320
cttcagtgga aggtaaacag aatctggtga ttatgggtag gaaaacctgg ttctccattc   1380
ctgagaagaa tcgaccttta aaggacagaa ttaatatagt tctcagtaga gaactcaaag   1440
aaccaccacg aggagctcat tttcttgcca aagtttgga tgatgcctta agacttattg    1500
aacaaccgga attggcaagt aaagtagaca tggtttggat agtcggaggc agttctgttt   1560
accaggaagc catgaatcaa ccaggccacc tcagactctt tgtgacaagg atcatgcagg   1620
aatttgaaag tgacacgttt ttcccagaaa ttgatttggg gaaatataaa cttctcccag   1680
aatacccagg cgtcctctct gaggtccagg aggaaaaagg catcaagtat aagtttgaag   1740
tctacgagaa gaaagactaa caggaagatg ctttcaagtt ctctgctccc ctcctaaagc   1800
tatgcatttt ttataagacc atgggacttt tgctggcttt agatcataat cagccatacc   1860
acatttgtag aggttttact tgctttaaaa aacctcccac acctcccct gaacctgaaa   1920 cataaaatga atgcaattgt tgttgttaac ttgtttattg cagcttataa tggttacaaa   1980
```

```
taaagcaata gcatcacaaa tttcacaaat aaagcatttt tttcactgca ttctagttgt    2040
ggtttgtcca aactcatcaa tgtatcttat catgtctgga tccccggcca acggtctggt    2100
gacccggctg cgagagctcg gtgtacctga gacgcgagta agcccttgag tcaaagacgt    2160
agtcgttgca agtccgcacc aggtactgat atcccaccaa aaagtgcggc ggcggctggc    2220
ggtagagggg ccagcgtagg gtggccgggg ctccgggggc gaggtcttcc aacataaggc    2280
gatgatatcc gtagatgtac ctggacatcc aggtgatgcc ggcggcggtg gtggaggcgc    2340
gcggaaagtc gcggacgcgg ttccagatgt tgcgcagcgg caaaaagtgc tccatggtcg    2400
ggacgctctg gccggtgagg cgtgcgcagt cgttgacgct ctagaccgtg caaaaggaga    2460
gcctgtaagc gggcactctt ccgtggtctg gtggataaat tcgcaagggt atcatggcgg    2520
acgaccgggg ttcgaacccc ggatccggcc gtccgccgtg atccatccgg ttaccgcccg    2580
cgtgtcgaac ccaggtgtgc gacgtcagac aacgggggag cgctccttt ggcttccttc     2640 caggcgcggc ggctgctgcg ctagcttttt tggcgagctc gaattaattc tgcattaatg    2700
aatcggccaa cgcgcgggga gaggcggttt gcgtattggg cgctcttccg cttcctcgct    2760
cactgactcg ctgcgctcgg tcgttcggct gcggcgagcg gtatcagctc actcaaaggc    2820
ggtaatacgg ttatccacag aatcagggga taacgcagga agaacatgt gagcaaaagg     2880 ccagcaaaag gccaggaacc gtaaaaaggc cgcgttgctg gcgttttcc ataggctccg     2940 cccccctgac gagcatcaca aaaatcgacg ctcaagtcag aggtggcgaa acccgacagg    3000
actataaaga taccaggcgt ttccccctgg aagctccctc gtgcgctctc ctgttccgac    3060
cctgccgctt accggatacc tgtccgcctt tctcccttcg ggaagcgtgg cgctttctca    3120
atgctcacgc tgtaggtatc tcagttcggt gtaggtcgtt cgctccaagc tgggctgtgt    3180
gcacgaaccc cccgttcagc ccgaccgctg cgccttatcc ggtaactatc gtcttgagtc    3240
caacccggta agacacgact tatcgccact ggcagcagcc actggtaaca ggattagcag    3300
agcgaggtat gtaggcggtg ctacagagtt cttgaagtgg tggcctaact acggctacac    3360
tagaaggaca gtatttggta tctgcgctct gctgaagcca gttaccttcg gaaaaagagt    3420
tggtagctct tgatccggca aacaaaccac cgctggtagc ggtggttttt ttgtttgcaa    3480
gcagcagatt acgcgcagaa aaaaaggatc tcaagaagat cctttgatct ttctacggg     3540 gtctgacgct cagtggaacg aaaactcacg ttaagggatt ttggtcatga gattatcaaa    3600
aaggatcttc acctagatcc ttttaaatta aaaatgaagt tttaaatcaa tctaaagtat    3660
atatgagtaa acttggtctg acagttacca atgcttaatc agtgaggcac ctatctcagc    3720
gatctgtcta tttcgttcat ccatagttgc ctgactcccc gtcgtgtaga taactacgat    3780
acgggagggc ttaccatctg gccccagtgc tgcaatgata ccgcgagacc cacgctcacc    3840
ggctccagat ttatcagcaa taaaccagcc agccggaagg gccgagcgca gaagtggtcc    3900
tgcaacttta tccgcctcca tccagtctat taattgttgc cgggaagcta gagtaagtag    3960
ttcgccagtt aatagtttgc gcaacgttgt tgccattgct acaggcatcg tggtgtcacg    4020
ctcgtcgttt ggtatggctt cattcagctc cggttcccaa cgatcaaggc gagttacatg    4080
atcccccatg ttgtgcaaaa aagcggttag ctccttcggt cctccgatcg ttgtcagaag    4140
taagttggcc gcagtgttat cactcatggt tatggcagca ctgcataatt ctcttactgt    4200
catgccatcc gtaagatgct tttctgtgac tggtgagtac tcaaccaagt cattctgaga    4260
atagtgtatg cggcgaccga gttgctcttg cccggcgtca atacgggata ataccgcgcc    4320
```

-continued

```
acatagcaga actttaaaag tgctcatcat tggaaaacgt tcttcggggc gaaaactctc      4380
aaggatctta ccgctgttga gatccagttc gatgtaaccc actcgtgcac ccaactgatc      4440
ttcagcatct tttactttca ccagcgtttc tgggtgagca aaaacaggaa ggcaaaatgc      4500
cgcaaaaaag ggaataaggg cgacacggaa atgttgaata ctcatactct tcctttttca      4560
atattattga agcatttatc agggttattg tctcatgagc ggatacatat ttgaatgtat      4620
ttagaaaaat aaacaaatag gggttccgcg cacatttccc cgaaaagtgc cacctgacgt      4680
ctaagaaacc attattatca tgacattaac ctataaaaat aggcgtatca cgaggccctt      4740
tcgtctcgcg cgtttcggtg atgacggtga aaacctctga cacatgcagc tcccggagac      4800
ggtcacagct tgtctgtaag cggatgccgg gagcagacaa gcccgtcagg gcgcgtcagc      4860
gggtgttggc gggtgtcggg gctggcttaa ctatgcggca tcagagcaga ttgtactgag      4920
agtgcaccat atgcggtgcg aaataccgca cagatgcgta aggagaaaat accgcatcag      4980
gcgccattcg ccattcaggc tgcgcaactg ttgggaaggg cgatcggtgc gggcctcttc      5040
gctattacgc cagctggcga aggggggatg tgctgcaagg cgattaagtt gggtaacgcc      5100
agggttttcc cagtcacgac gttgtaaaac gacggccagt gccaagcttt ttgca          5155
```

<210> SEQ ID NO 4
<211> LENGTH: 4886
<212> TYPE: DNA
<213> ORGANISM: Homo sapiens

<400> SEQUENCE: 4

```
ctagcatgca gtcaagctta catcagactt cgacaaccca agatggattg gacgacacaa        60
gcatatgttc aatttccttg atgtcaacca caatggaaaa atctctcttg acgagatggt       120
ctacaaggca tctgatattg tcatcaataa ccttggagca cacctgagc aagccaaacg        180 acacaaagat gctgtagaag ccttcttcgg aggagctgga atgaaatatg gtgtggaaac       240
tgattggcct gcatatattg aaggatggaa aaaattggct actgatgaat ggagaaaata       300
cgccaaaaac gaaccaacgc tcatccgtat atggggtgat gctttgtttg atatcgttga       360
caaagatcaa aatggagcca ttacactgga tgaatggaaa gcatacacca agctgctgg        420 tatcatccaa tcatcagaag attgcgagga acattcaga gtgtgcgata ttgatgaaag        480
tggacaactc gatgttgatg agatgacaag acaacattta ggattttggt acaccatgga       540
tcctgcttgc gaaaagctct acggtggagc tgtcccctaa gaagaattca aaaagcttct       600
cgagagtact tctagagcgg ccgcgggccc atcgatttc cacccgggtg ggtaccagg        660 taagtgtacc caattcgccc tatagtgagt cgtattacaa ttcactggcc gtcgttttac       720
aacgtcgtga ctgggaaaac cctggcgtta cccaacttaa tcgccttgca gcacatcccc       780
ctttcgccag ctggcgtaat agcgaagagg cccgcaccga tcgcccttcc caacagttgc       840
gcagcctgaa tggcgaatgg agatccaatt tttaagtgta taatgtgtta aactactgat       900
tctaattgtt tgtgtatttt agattcacag tcccaaggct catttcaggc ccctcagtcc       960
tcacagtctg ttcatgatca taatcagcca taccacattt gtagaggttt tacttgcttt      1020
aaaaaacctc ccacacctcc ccctgaacct gaaacataaa atgaatgcaa ttgttgttgt      1080
taacttgttt attgcagctt ataatggtta caaataaagc aatagcatca caaatttcac      1140
aaataaagca tttttttcac tgcattctag ttgtggtttg tccaaactca tcaatgtatc      1200
ttaacgcgta aattgtaagc gttaatattt tgttaaaatt cgcgttaaat ttttgttaaa      1260
tcagctcatt ttttaaccaa taggccgaaa tcggcaaaat cccttataaa tcaaaagaat      1320
```

-continued

```
agaccgagat agggttgagt gttgttccag tttggaacaa gagtccacta ttaaagaacg    1380
tggactccaa cgtcaaaggg cgaaaaaccg tctatcaggg cgatggccca ctacgtgaac    1440
catcacccta atcaagtttt ttggggtcga ggtgccgtaa agcactaaat cggaacccta    1500
aagggagccc ccgatttaga gcttgacggg gaaagccggc gaacgtggcg agaaaggaag    1560
ggaagaaagc gaaaggagcg ggcgctaggg cgctggcaag tgtagcggtc acgtgcgcg    1620 taaccaccac acccgccgcg cttaatgcgc cgctacaggg cgcgtcaggt ggcacttttc    1680
ggggaaatgt gcgcggaacc cctatttgtt tatttttcta aatacattca aatatgtatc    1740
cgctcatgag acaataaccc tgataaatgc ttcaataata ttgaaaaagg aagagtcctg    1800
aggcggaaag aaccagctgt ggaatgtgtg tcagttaggg tgtggaaagt ccccaggctc    1860
cccagcaggc agaagtatgc aaagcatgca tctcaattag tcagcaacca ggtgtggaaa    1920
gtccccaggc tccccagcag gcagaagtat gcaaagcatg catctcaatt agtcagcaac    1980
catagtcccg cccctaactc cgcccatccc gcccctaact ccgcccagtt ccgcccattc    2040
tccgccccat ggctgactaa ttttttttat ttatgcagag gccgaggccg cctcggcctc    2100
tgagctattc cagaagtagt gaggaggctt ttttggaggc ctaggctttt gcaaagatcg    2160
atcaagagac aggatgagga tcgtttcgca tgattgaaca agatggattg cacgcaggtt    2220
ctccggccgc ttgggtggag aggctattcg gctatgactg ggcacaacag acaatcggct    2280
gctctgatgc cgccgtgttc cggctgtcag cgcaggggcg cccggttctt tttgtcaaga    2340
ccgacctgtc cggtgccctg aatgaactgc aagacgagga gcgcggcta tcgtggctgg    2400 ccacgacggg cgttccttgc gcagctgtgc tcgacgttgt cactgaagcg ggaagggact    2460
ggctgctatt gggcgaagtg ccggggcagg atctcctgtc atctcacctt gctcctgccg    2520
agaaagtatc catcatggct gatgcaatgc ggcggctgca tacgcttgat ccggctacct    2580
gcccattcga ccaccaagcg aaacatcgca tcgagcgagc acgtactcgg atggaagccg    2640
gtcttgtcga tcaggatgat ctggacgaag agcatcaggg gctcgcgcca gccgaactgt    2700
tcgccaggct caaggcgagc atgcccgacg gcgaggatct cgtcgtgacc catggcgatg    2760
cctgcttgcc gaatatcatg gtggaaaatg gccgcttttc tggattcatc gactgtggcc    2820
ggctgggtgt ggcggaccgc tatcaggaca tagcgttggc tacccgtgat attgctgaag    2880
agcttggcgg cgaatgggct gaccgcttcc tcgtgcttta cggtatcgcc gctcccgatt    2940
cgcagcgcat cgccttctat cgccttcttg acgagttctt ctgagcggga ctctggggtt    3000
cgaaatgacc gaccaagcga cgcccaacct gccatcacga gatttcgatt ccaccgccgc    3060
cttctatgaa aggttgggct tcggaatcgt tttccgggac gccggctgga tgatcctcca    3120
gcgcggggat ctcatgctgg agttcttcgc ccaccctagg gggaggctaa ctgaaacacg    3180
gaaggagaca ataccggaag gaacccgcgc tatgacggca ataaaagac agaataaaac    3240 gcacggtgtt gggtcgtttg ttcataaacg cggggttcgg tcccagggct ggcactctgt    3300 cgataccccca ccgagacccc attggggcca atacgcccgc gtttcttcct tttcccacc    3360 ccaccccca agttcgggtg aaggcccagg gctcgcagcc aacgtcgggg cggcaggccc    3420
tgccatagcc tcaggttact catatatact ttagattgat ttaaaacttc attttaatt    3480 taaaaggatc taggtgaaga tcctttttga taatctcatg accaaaatcc cttaacgtga    3540
gttttcgttc cactgagcgt cagacccccgt agaaaagatc aaaggatctt cttgagatcc    3600 ttttttctg cgcgtaatct gctgcttgca aacaaaaaaa ccaccgctac cagcggtggt    3660
```

-continued

```
ttgtttgccg gatcaagagc taccaactct ttttccgaag gtaactggct tcagcagagc      3720
gcagatacca aatactgtcc ttctagtgta gccgtagtta ggccaccact tcaagaactc      3780
tgtagcaccg cctacatacc tcgctctgct aatcctgtta ccagtggctg ctgccagtgg      3840
cgataagtcg tgtcttaccg ggttggactc aagacgatag ttaccggata aggcgcagcg      3900
gtcgggctga acgggggtt cgtgcacaca gcccagcttg gagcgaacga cctacaccga      3960
actgagatac ctacagcgtg agctatgaga aagcgccacg cttcccgaag ggagaaaggc      4020
ggacaggtat ccggtaagcg gcagggtcgg aacaggagag cgcacgaggg agcttccagg      4080
gggaaacgcc tggtatcttt atagtcctgt cgggtttcgc cacctctgac ttgagcgtcg      4140
atttttgtga tgctcgtcag gggggcggag cctatggaaa aacgccagca acgcggcctt      4200
tttacggttc ctggcctttt gctggccttt tgctcacatg ttctttcctg cgttatcccc      4260
tgattctgtg gataaccgta ttaccgccat gcattagtta ttaatagtaa tcaattacgg      4320
ggtcattagt tcatagccca tatatggagt tccgcgttac ataacttacg gtaaatggcc      4380
cgcctggctg accgcccaac gacccccgcc cattgacgtc aataatgacg tatgttccca      4440
tagtaacgcc aatagggact ttccattgac gtcaatgggt ggagtattta cggtaaactg      4500
cccacttggc agtacatcaa gtgtatcata tgccaagtac gccccctatt gacgtcaatg      4560
acggtaaatg gcccgcctgg cattatgccc agtacatgac cttatgggac tttcctactt      4620
ggcagtacat ctacgtatta gtcatcgcta ttaccatggt gatgcggttt tggcagtaca      4680
tcaatgggcg tggatagcgg tttgactcac ggggatttcc aagtctccac cccattgacg      4740
tcaatgggag tttgttttgg caccaaaatc aacgggactt tccaaaatgt cgtaacaact      4800
ccgccccatt gacgcaaatg ggcggtaggc gtgtacggtg ggaggtctat ataagcagag      4860
ctggtttagt gaaccgtcag atccga                                          4886
```

VANILLOID RECEPTOR

This is a continuation of Ser. No. 09/533,220, Mar. 23, 2000, now U.S. Pat. No. 6,406,908

The present invention is directed to an isolated nucleic acid encoding human vanilloid receptor, said receptor, its preparation, cells expressing said receptor and an assay for testing compounds for their potential to decrease pain in humans.

More particularly the present invention provides in a first aspect, an isolated nucleic acid encoding a human vanilloid receptor.

Even more particularly the present invention provides an isolated nucleic acid capable of directing expression of a human vanilloid receptor, in particular a cDNA capable of directing expression of said receptor, more particularly a cDNA comprising the nucleotide sequence as depicted in SEQ ID NO:1, most particularly a cDNA capable of directing expression of the predicted protein depicted in SEQ ID NO:2.

Said isolated nucleic acid may have a nucleotide sequence having sequence identity within a range of from more than 85.5%, preferably more than 97% to 100% over the open reading frame with the nucleotide sequence as described in SEQ ID NO:1. Preferably said isolated nucleic acid comprises a nucleic acid identical over the open reading frame to the sequence as described in SEQ ID NO:1.

The nucleic acid may be prepared for example by constructing a cDNA library from mRNA derived from human neuronal cells expressing vanilloid receptor. Such cells may be the nociceptive neurones, the cell bodies thereof residing within the dorsal root ganglia. The cDNA may then be expressed in a cell line not normally expressing endogenous vanilloid receptor and by iteratively subdividing and reassaying positive clones an individual clone may be obtained comprising the desired nucleic acid.

In a further embodiment the present invention is directed to a recombinant human vanilloid receptor. An example for said human vanilloid receptor may be a protein encoded by a nucleic acid having sequence identity within a range of from more than 85.5%, preferably more than 97% to 100% over the open reading frame with the nucleotide sequence as described in SEQ ID NO:1, e.g. a protein comprising an amino acid sequence having sequence identity within a range of from more than 85.7% to 100% with the amino acid sequence as described in SEQ ID NO:2, as calculated using the ALIGN program [Myers and Miller, CABIOS (1989)]. The amino acid differences may occur at a site selected from the N-terminus, the C-terminus and the putative pore region of the channel, i.e. amino acid 597 to amino acid 696 of SEQ ID NO:2. Preferably the human vanilloid receptor comprises an amino acid sequence identical to the sequence as described in SEQ ID NO:2.

The human vanilloid receptor when expressed in mammalian cells is activated by capsaicin, temperatures greater than 42° C. and by pH less than 5.5. The activation by all these effectors can be blocked substantially or completely by the action of the capsaicin antagonist capsazepine.

The vanilloid receptor may be prepared by stably transfecting a cell line with an appropriate expression cassette comprising a nucleic acid encoding the receptor, and culturing cells of said cell line under conditions which allow expression of said receptor.

In a further embodiment the present invention is directed to a cell belonging to a cell line expressing recombinant human vanilloid receptor.

In a further embodiment the present invention is directed to a cell belonging to a cell line expressing recombinant mammalian vanilloid receptor and aequorin.

Examples for useful cell lines include any cell line growing well in culture, e.g. human embryonic kidney derived cells, like HEK293 cells and Chinese hamster ovary cells, like CHO-DUKX-B11 cells [Kaufman et al., Mol. Cell biol. 5:1750–1759 (1985)], which have been transformed/transfected with an appropriate expression cassette comprising a nucleic acid encoding human or mammalian vanilloid receptor and optionally a nucleic acid encoding aequorin. The expression cassette may be derived from a vector selected from for example pIRESneo, pBKCMV and pXMT3. A very useful cell line is the CHO-DUKX-B11 cell line.

Examples for a mammalian vanilloid receptor are the rat receptor and the human receptor.

Aequorin is a protein from the jellyfish. In the presence of $Ca^{++}$ ions the complex of aequorin and coelenterazine gives off light.

In a further embodiment the present invention is directed to an assay to measure vanilloid receptor activation comprising measuring changes in aequorin luminescence of cells expressing a mammalian vanilloid receptor and aequorin.

In a further embodiment the present invention is directed to a screening assay for vanilloid receptor channel blockers comprising incubation of a cell expressing a mammalian vanilloid receptor and aequorin with the potential vanilloid receptor channel blocker, adding an activator/agonist, e.g. capsaicin, of the vanilloid receptor channel and measuring changes in aequorin luminescence.

In a further embodiment the present invention is directed to a screening assay for vanilloid receptor channel agonists comprising incubation of a cell expressing a mammalian vanilloid receptor and aequorin, adding the potential vanilloid receptor channel agonist and measuring changes in aequorin luminescence.

In a further embodiment the present invention is directed to an assay to measure vanilloid receptor activation comprising measuring changes in the fluorescence of laser activated, calcium sensitive dyes, e.g. fura 2 AM and fluo3.

In a further embodiment the present invention is directed to a screening assay for vanilloid receptor channel blockers comprising incubation of a cell expressing a mammalian vanilloid receptor and optionally aequorin with the potential vanilloid receptor channel blocker, adding an activator/agonist, e.g. capsaicin, of the vanilloid receptor and measuring changes in the fluorescence of laser activated, calcium sensitive dyes, e.g. fura 2 AM and fluo 3.

In a further embodiment the present invention is directed to a screening assay for vanilloid receptor channel agonists comprising incubation of a cell expressing a mammalian vanilloid receptor and optionally aequorin with the potential vanilloid receptor channnel agonist and measuring changes in the fluorescence of laser activated, calcium sensitive dyes, e.g. fura 2 AM and fluo3.

The above assay formats allow automation and are suitable for screening.

In a further embodiment the present invention is directed to a novel vanilloid receptor channel blocker identified by a screening assay for vanilloid receptor channel blockers comprising incubation of a cell expressing a mammalian vanilloid receptor and aequorin with the potential vanilloid receptor channel blocker, adding an activator/agonist, e.g. capsaicin, of the vanilloid receptor and measuring changes in aequorin luminescence.

In a further embodiment the present invention is directed to a novel vanilloid receptor channel agonist identified by a screening assay for vanilloid receptor channel agonists comprising incubation of a cell expressing a mammalian vanilloid receptor and aequorin with the potential vanilloid receptor channel agonist and measuring changes in aequorin luminescence.

In a further embodiment the present invention is directed to a novel vanilloid receptor channel blocker identified by a screening assay for vanilloid receptor channel blockers comprising incubation of a cell expressing a mammalian vanilloid receptor and optionally aequorin with the potential vanilloid receptor channel blocker, adding an activator/agonist, e.g. capsaicin, of the vanilloid receptor and measuring changes in the fluorescence of laser activated, calcium sensitive dyes, e.g. fura 2 AM and fluo3.

In a further embodiment the present invention is directed to a novel vanilloid receptor channel agonist identified by a screening assay for vanilloid receptor channel agonists comprising incubation of a cell expressing a mammalian vanilloid receptor and optionally aequorin with the potential vanilloid receptor channel agonist and measuring changes in the fluorescence of laser activated, calcium sensitive dyes, e.g. fura 2 AM and fluo3.

In accordance with the foregoing the present invention also provides:
(1) an isolated nucleic acid encoding a human vanilloid receptor;
(2) a recombinant human vanilloid receptor;
(3) a method of preparation of the receptor of (2);
(4) a cell line expressing the receptor of (2) and optionally aequorin;
(5) an assay to measure vanilloid receptor activation;
(6) a screening assay for vanilloid receptor channel blockers or agonists; and
(7) novel vanilloid receptor channel blocker or agonist, e.g. obtained via (6).

The following examples illustrate the invention without limitation. The following abbreviations are used in the examples: DRG: dorsal root ganglion; G418: Geneticin; HBSS: Hanks balanced salt solution; PBS: phosphate buffered saline; RT: room temperature; VR: vanilloid receptor

EXAMPLE A1

Preparation of CHO Cells Expressing Rat VR and Aequorin (a) Aequorin-pXMT3: The pXMT3 mammalian expression plasmid, SEQ ID NO:3, encodes a cDNA for dihydrofolate reductase. Aequorin-pBk-CMV (SEQ ID NO:4) is linearised with Nhe1 (immediately upstream of the Kozak consensus sequence). The 5'overhang is filled in with Klenow fragment and phosphorylated PstI linker (New England Biolabs) is blunt end ligated to the DNA. The aequorin insert is released with PstI and EcoRI and cloned into pXMT3.

(b) Cloning of rVR1: A rat vanilloid receptor, rVR1, cDNA is cloned by homology cloning from a rat DRG cDNA library in lambda ZAP express using a 969 bp PCR fragment corresponding to nucleotides 1513 to 2482 from the rat VR1 sequence [Caterina et al., Nature 389:816–824 (1997)] as a probe. This probe is derived by RT-PCR using RNA from adult rat DRG [Helliwell et al., Neuroscience Lett. 250:177–180 (1998). The rVR1 insert is then cut out with EcoR1 and Not1 and then subcloned into the pIRESneo expression vector (Accession Number U89673) (Clontech).The rVR1 PCR clone is then subcloned into pcDNA3.1 (Invitrogen) expression vector. DNA used for transient and stable transfections is purified using Promega's Wizard plus Maxi or Megaprep DNA purification systems.

(c) Production of rVR1/aequorin CHO cell stable clone: DUKX-CHO-Aequorin cells which have previously been transfected with pXMT3-aequorin are transfected with pIRESneo-rVR1 using LipofectAMINE PLUS reagent. 1,000,000 cells are transfected with 1.25 $\mu$g of rVR1 DNA. 2 days following transfectection 700 $\mu$g/ml G418 is used to select for positive cells. Transfected cells are visible after 5 days and continued to be grown in the presence of G418 after that. 10 days later the G418 selected cells are cloned by limiting dilution in 96 well plates and continue to be grown in G418 after that.

EXAMPLE A2

Preparation of CHO Cells Expressing Human VR and Aequorin (a) Cloning of hVR1: A human DRG cDNA library of approximately 80,000 clones is made in lambda ZAP express using a Stratagene kit. The library is screened at low stringency (2×SSC, 45° C.) using the rat VR1 probe described in Example A1. Several clones are isolated and the longest full-length one, clone 3D, is chosen for expression studies (SEQ ID NO:1). The insert is cut out with Eco R1 and Not 1 and cloned into pIRESneo (Accession Number U89673) (Clontech).

(b) Production of hVR1/Aequorin CHO cell stable clone: DUKX-CHO-Aequorin cells which have previously been transfected with pXMT3-aequorin are transfected with pIRESneo-hVR1 using LipofectAMINE PLUS reagent. 1,000,000 cells are transfected with 1.25 $\mu$g of hVR1 DNA. 2 days following transfection 700 $\mu$g/ml G418 is used to select for positive cells. Transfected cells are visible after 5 days and later, the G418 selected cells are cloned by limiting dilution in 96 well plates and continue to be grown in the presence of G418 after that.

EXAMPLE B1

Potency of Capsaicin (Agonist)

(a) Calcium uptake assay: Primary cultures of adult DRG neurones are prepared according to standard protocols [Wood et al., J. Neuroscience 8:3208–3220 (1988)]. Cells are plated at a density of 2000 per well on 96 well view plates pre-coated with poly-ornithine and laminin and cultured in Hams F14 supplemented with 100 ng/ml NGF for four days. On the day of the assay, the cells are washed eight times in a Denley cell washer with calcium/magnesium free HBSS plus 10 mM HEPES, pH7.4. After washing the wells contain approximately 75 $\mu$l of buffer. To this is added 25 $\mu$l of capsaicin with or without capsazepine or ruthenium red in Ca/Mg free buffer containing 370 KBq of $^{45}Ca^{2+}$/ml. For negative control, capsaicin is omitted. Samples are incubated at RT for 10 min, then washed four times with HBSS/10 mM HEPES pH 7.4. The remaining buffer is removed from the wells and replaced with 25 $\mu$l of 0.1% SDS. After about 10 min 200 $\mu$l of Microscint 40 scintillant is added and samples are counted on a Packard Topcount.

(b) Measurement of aequorin activity: Active aequorin is reconstituted by incubating confluent cells resulting from Examples A1 or A2 at 37° C. with 20 μM coelenterazine h [Biochem. J. 261:913–920 (1989)] and 30 μM glutathione (reduced form) in 50 μl of medium per well. All the plates for use in a day are set up at the same time. The first plate is used in the assay after 2.5 h incubation with coelenterazine h. Subsequent plates are used at about 10 min intervals. There is no loss of signal with the longer incubation times. At the start of the assay, the medium containing coelenterazine h is removed and replaced with 100 μl of HBSS buffered to pH 7.4 with 10 mM HEPES containing test compounds where appropriate. Cells are incubated for at least 10 min at RT. They are then placed in the measuring chamber of a luminometer (Wallac Microbeta Jet). Agonist is injected in a volume of 20 μl HBSS and the luminescence signal is collected for 20 sec.

(c) Fluorometric assay using the FLIPR: Cells resulting from Examples A1 or A2 are plated at a density of 50,000 cells/well in Costar Viewplates. The cells are incubated at 37° C. in a humidified atmosphere (5% $CO_2$/95% air) for 24 h. Medium is removed by flicking the plates and replaced with 100 μl HBSS containing 2 μM Fluo-3, AM (Molecular Probes) in the presence of 2.5 mM probenicid (Sigma) and 0.02% pluronic acid (Molecular Probes). The cells are incubated at 37° C. in a humidified atmosphere (5% $CO_2$/95% air) for 1 h. Plates are flicked to remove excess of Fluo-3, AM, washed twice with HBSS and refilled with 100 μl of HBSS containing screening compounds. Incubation in the presence of screening compounds lasts between 10 and 20 min. Plates are then placed in the cell plate stage of the FLIPR (Molecular Devices, Sunnyvale, Calif., USA). A baseline consisting in 5 measurements of 0.4 sec each (laser: excitation 488 nm at 0.6 W, CCD camera opening of 0.4 sec) is recorded. Capsaicin (50 μl at 45 nM) is added from the agonist plate (placed in the agonist plate stage of the FLIPR tower) to the cell plate using the FLIPR 96-tip pipettor simultaneously to fluorescence recording for 3 min according to the following scheme: 0.4 sec measurements each interval of 1 sec for 1 min followed by 0.4 sec measurements each interval of 4 sec for 100 sec. Data are expressed as (Fm−Fb)/Fb where Fm is the fluorescence peak reached following capsaicin injection and Fb is the baseline fluorescence prior to capsaicin injection.

| $EC_{50}$ (nM) (aequorin assay) | | $EC_{50}$ (nM) | $EC_{50}$ (nM) |
|---|---|---|---|
| rVR1 in CHO cells | hVR1 in CHO cells | (Ca uptake assay) Rat DRG neurones | (Fluo-3 assay) hVR1 in CHO cells |
| 530 ± 110 | 480 ± 64 | 170 ± 19 | 3.42 ± 0.2 |

EXAMPLE B2

Capsazepine and Ruthenium Red Activity on Vanilloid Receptors Activated by Capsaicin (a) Inhibition of capsaicin responses by the competitive antagonist, capsazepine, is measured as described in Example B1. Capsaicin is used at a concentration of 1 μM. The $IC_{50}$ for capsazepine at hVR1 is comparable to that at rVR1 and slightly lower than that measured in calcium uptake assays with DRG neurones.

(b) Activity of the channel blocker ruthenium red is measured as described in Example B1. The layout and conditions are the same as for (a) above. Ruthenium red is an effective blocker of capsaicin responses. The $IC_{50}$ at hVR1 is slightly higher than at the cloned rVR1 or that found in the calcium uptake assay with primary cultures of DRG neurones.

| Compound | $IC_{50}$ (nM) (aequorin assay) | | $IC_{50}$ (nM) | $IC_{50}$ (nM) |
|---|---|---|---|---|
| | rVR1 (CHO) | hVR1 (CHO) | (Ca uptake assay) Rat DRG neurones | (Fluo-3 assay) hVR1 CHO |
| Cz | 320 ± 110 | 120 ± 12 | 800 ± 40 | 130 ± 32 |
| Rr | 18 ± 8.3 | 220 ± 32 | 50* | |

*From Wood et al (1988)
Cz: Capsazepine;
Rr: Ruthenium red;
(CHO): in CHO cells3

What is claimed is:

1. A recombinant human vanilloid receptor comprising an 40 amino acid sequence identical to the sequence of SEQ ID NO:2.

* * * * *